United States Patent
Bouchée et al.

[11] Patent Number: 5,186,896
[45] Date of Patent: Feb. 16, 1993

[54] CUVETTE ROTOR

[75] Inventors: Bernhard Bouchée, Hofheim am Taunus; Karl Fickenscher, Marburg, both of Fed. Rep. of Germany

[73] Assignee: Behringwerke Aktiengesellschaft, Marburg, Fed. Rep. of Germany

[21] Appl. No.: 530,310

[22] Filed: May 30, 1990

[30] Foreign Application Priority Data

Jun. 1, 1989 [DE] Fed. Rep. of Germany ....... 3917866

[51] Int. Cl.$^5$ ........................................... G01N 21/07
[52] U.S. Cl. ....................................... 422/72; 422/64; 422/102; 436/45; 436/177; 436/180
[58] Field of Search ............................ 422/64, 72, 102; 436/45, 177, 180; 356/246

[56] References Cited

U.S. PATENT DOCUMENTS

| | | | |
|---|---|---|---|
| 4,314,970 | 2/1982 | Stein et al. | 422/72 |
| 4,456,581 | 6/1984 | Edelmann et al. | 422/72 |
| 4,580,897 | 4/1986 | Nelson et al. | 356/246 |
| 4,580,898 | 4/1986 | Keramaty et al. | 356/246 |
| 4,902,479 | 2/1990 | Brikus | 422/72 |

FOREIGN PATENT DOCUMENTS

| | | |
|---|---|---|
| 0163038 | 12/1985 | European Pat. Off. . |
| 3340505 | 5/1985 | Fed. Rep. of Germany ...... 356/246 |

Primary Examiner—Robert J. Warden
Assistant Examiner—Timothy M. McMahon
Attorney, Agent, or Firm—Finnegan, Henderson, Farabow, Garrett and Dunner

[57] ABSTRACT

The invention relates to a cuvette rotor having at least one radially extending cuvette with a first chamber, a second chamber and a third chamber, the first chamber being located at a central location on the rotor, the third chamber being located at a peripheral location on the rotor, and the second chamber being located between the first and third chambers. The cuvette is defined by a top wall, a bottom wall, and side walls. A first barrier defines a boundary between the first and second chambers, and a second barrier defines a boundary between the second and third chambers. First, second and third ports are disposed in the top wall of the cuvette above the first, second and third chambers, respectively, and a first deflector is disposed between the first and second ports and connected to the top wall of the cuvette. Similarly, a second deflector is disposed between the second and third ports and is connected to the top wall of the cuvette. Finally, at least one vessel having top and bottom walls is arranged on the rotor adjacent the cuvette, the vessel being separated from the cuvette by a side wall, and the top wall of the vessel including a fourth port.

9 Claims, 2 Drawing Sheets

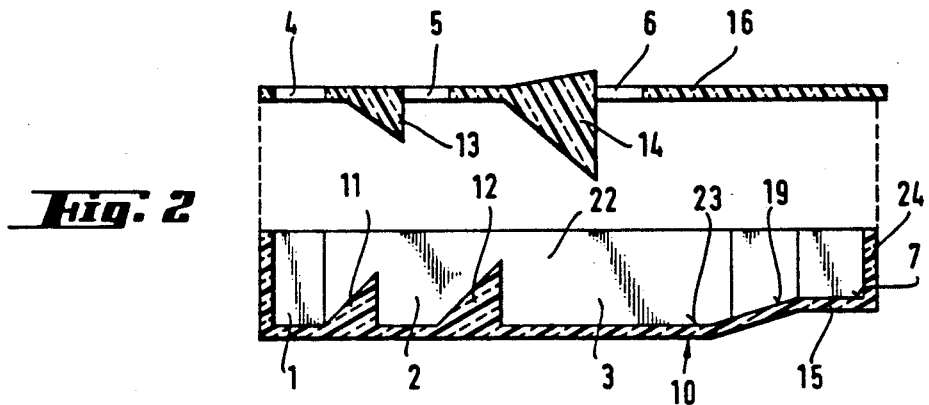
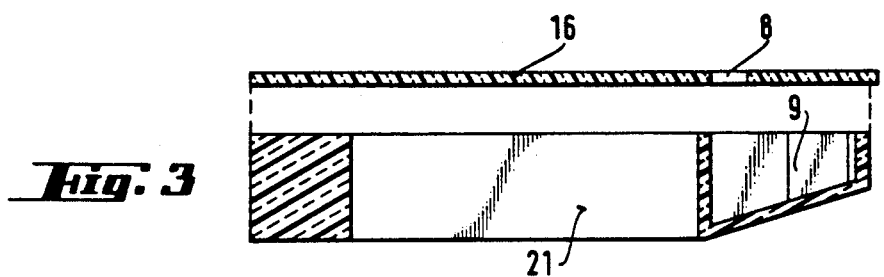
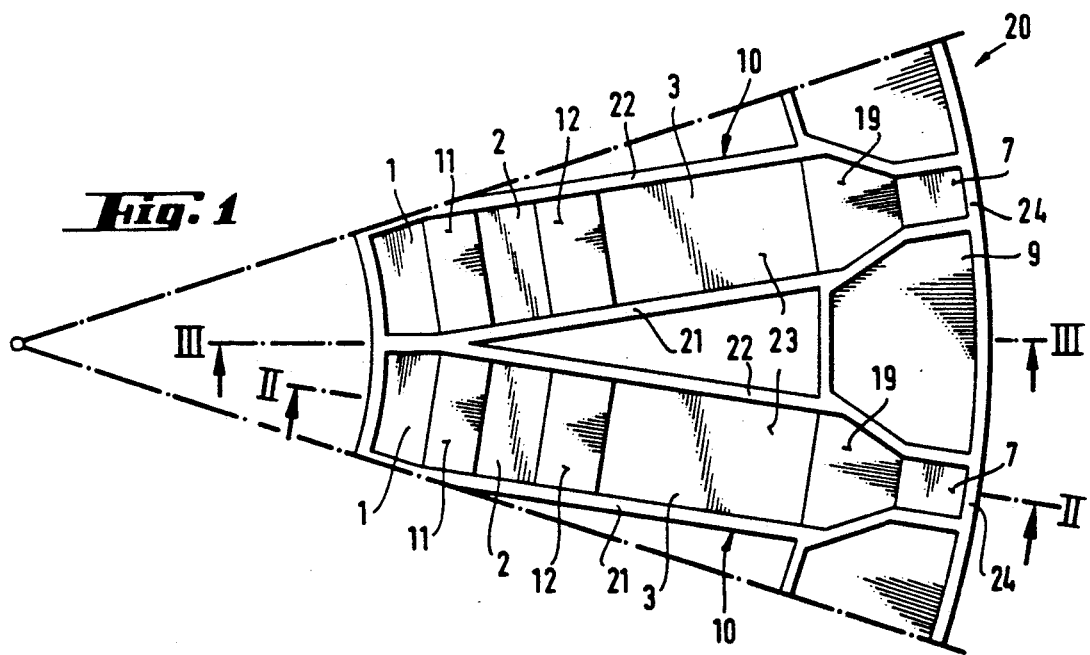

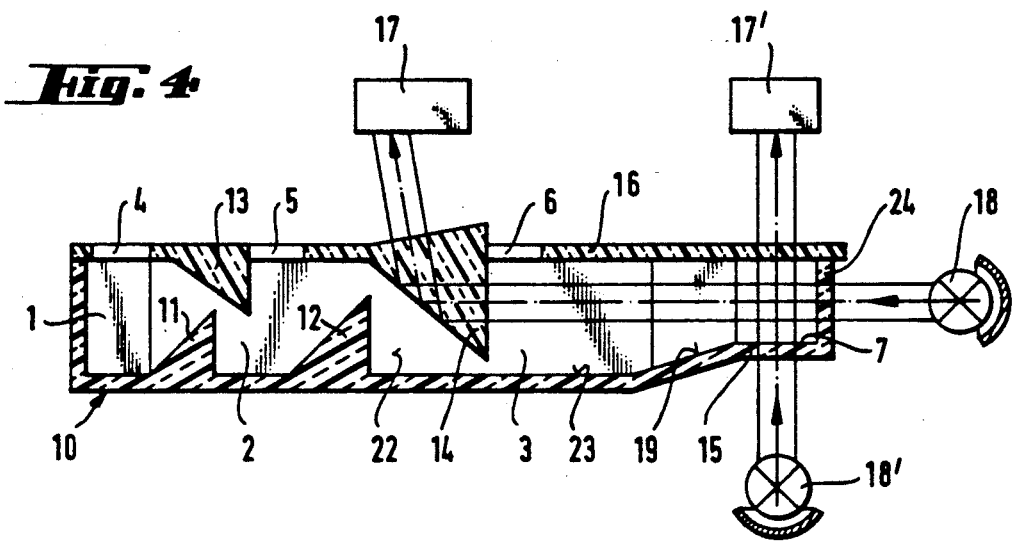
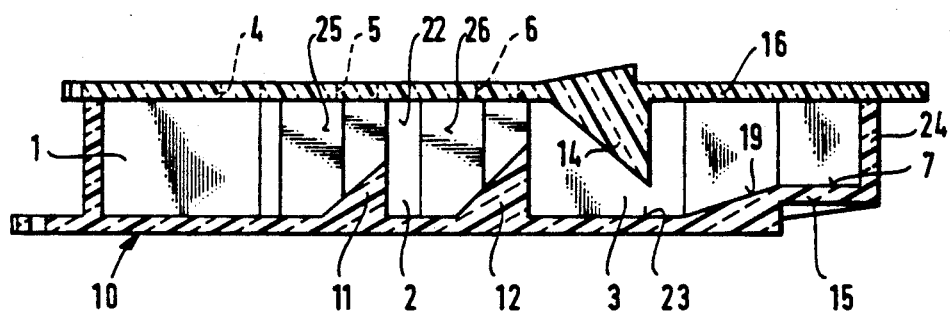
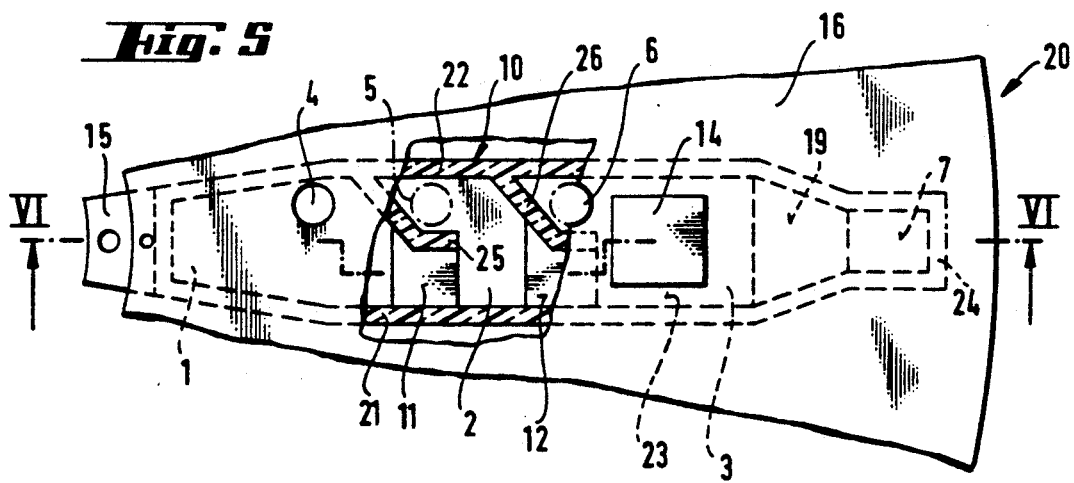

CUVETTE ROTOR

BACKGROUND OF THE INVENTION

1. Field of the Invention

The invention relates to a cuvette rotor which has separate radially arranged cuvettes and can be employed in automatically operating centrifugal analysis systems for investigating biological fluids such as, for example, blood, blood plasma or blood serum.

2. Description of the Related Art

Before the analysis, the biological fluids are, where appropriate, diluted and, for determining particular properties or constituents, mixed with specific reagents as are required, for example, for PT, aPTT, fibrinogen, factor II-XII tests, and the reaction result is detected optically.

A cuvette rotor for such analyses is disclosed in European Patent Application 0,163,038. The separate, circularly arranged cuvettes extend radially and are closed on all sides. They each have two chambers which are separated from one another by a barrier and are provided with an opening for filling. Biological fluid is placed in the chamber arranged toward the axis of rotation, a specific reagent and, where appropriate, a diluent are placed in the peripherally arranged chamber. The contents of the two chambers when, owing to the action of the centrifugal forces, the biological fluid passes over the barrier into the peripherally arranged chamber. Optical measurement takes place at right angles to the plane of the rotor with a fixed path length of the fluid to be analyzed.

SUMMARY OF THE INVENTION

The invention has the object of providing a cuvette rotor in which each cuvette has three chambers and there is the option of subjecting the reaction mixture to photometry both at a given fixed and at a variable path length. Furthermore, the intention is to arrange on the rotor other chambers, independent of the separate cuvettes, for dilution of samples. The object is achieved by a cuvette rotor wherein the cuvettes are bounded in their radial dimension by side walls which are essentially parallel to one another and by an upper part and a lower part, and have three chambers separated by barriers arranged on the lower part, there being, projecting into the central and into the peripherally arranged chamber, in each case at least one deflector fixed to the upper part. A vessel which is closed on all sides is formed between each of the separate cuvettes and its interior is connected to an opening in the upper part.

The peripherally arranged chambers can have sections of different cross-section located one behind the other in the radial direction, with the cross-section of the section located at the periphery being the smallest. The deflectors projecting into the peripherally arranged chambers can be designed as deviation devices for light. It is furthermore possible for the peripherally arranged chambers to be separated from the central chambers by two barriers which face one another at a small distance. In another embodiment, the chambers are separated from one another by partitions which cover at least half the width of the chambers and by barriers which are arranged between the partitions and the side walls.

The principle advantages of the invention are that samples and reagents can be introduced separately, the rotor has vessels for diluting the samples, which are in a space-saving arrangement between the cuvettes, and the path length for the transmitted beam can be increased when the extinctions are low.

The cuvette rotor is explained in more detail hereinafter by means of drawings which represent merely one embodiment.

BRIEF DESCRIPTION OF THE DRAWINGS

FIG. 1 is a top view of a segment of the cuvette rotor in accordance with the present invention;

FIG. 2 shows the section II—II of FIG. 1 with the upper part;

FIG. 3 shows the section III—III of FIG. 1 with the upper part;

FIG. 4 shows a measuring arrangement for measurement with a fixed path length or variable path in accordance with the invention;

FIG. 5 shows a top view of a second embodiment of a single cuvette in accordance with the present invention and FIG. 6 is a cross-sectional view taken along line VI—VI of FIG. 5.

DESCRIPTION OF THE PREFERRED EMBODIMENTS

As shown in FIG. 1, the cuvette rotor 20 comprises cuvettes 10 which are closed on all sides and are bounded by walls 21, 22 which are essentially parallel to one another, and by an upper part 16 and a lower part 15, shown in FIG. 2. The separate cuvettes 10 each have three chambers 1, 2, 3 which are separated from one another by barriers 11, 12. The barriers 11, 12 are arranged on the lower part 15. The barriers 11, 12 are designed so that, on the one hand, at the required chamber volume no overflow into the adjacent chamber can take place and, on the other hand, on centrifugation there is formation of a breakaway edge which has a beneficial effect on the mixing of the reactants. The upper part 16 is provided with openings 4, 5, 6 through which the interior of the chambers 1, 2, 3 is accessible. Furthermore, deflectors 13, 14 are arranged on the upper part 16 (FIG. 2) and project into the central chamber 2 and into the peripherally arranged chamber 3. The deflectors 13, 14 prevent fluid which is running along the underside of the upper part 16 from emerging through the openings 5 and 6. Moreover, further breakaway edges are produced and have a beneficial effect on the mixing of the reactants. The space between the individual cuvettes 10 is designed as closed vessel 9 for dilution of the samples. Its interior is accessible via opening 8 in the upper part 16 (FIG. 3). In order to keep the amount of sample small, the peripherally arranged chamber 3 can have sections 7, 19 and 23 of different cross-section, with the cross-section of section 7 being only a fraction of the cross-section of section 23. The reduction in cross-section is essentially achieved by tapering the section 19 in the peripheral direction. In section 7 the walls 21, 23 and the upper and lower part are again aligned parallel to one another. Section 7 is used as measuring space for a constant path length of the sample on axial measurement and a variable path length on radial measurement (FIG. 4). In the region of section 7 the upper part 16 and lower part 15, and the front wall 24, of the cuvettes 10 are designed as optical windows. It is furthermore possible for the deflector 14 to be designed as deviation device for light. The path of the light ray for the measurement in the axial and radial direction is depicted in FIG. 4. 18 and 18' indicate the light emitters, 17 and 17' indicate the light receivers and 14 indicates the deflector designed as deviation device for light. It is, of course, also possible to interchange the light emitters and light receivers. To improve the mixing of the reactants, the peripherally arranged chamber 3 can be separated from the central chamber 2 by two barriers which face one another at a small distance. The rotary movement of the cuvette rotor causes the reactants, which are initially separate, to move radially in the direction of the front wall 24, thereby to flow over the barriers 11, 12 and to mix with one another. Finally, the mixture fills section 7 of the cuvette 10.

In the embodiment shown in FIGS. 5 and 6, the chambers 1, 2, 3 are separated from one another by partitions 25, 26, which extend over at least half the width of the chamber, and barriers 11, 12. The walls 25, 26 prevent any possibility of fluid emerging out of the chambers 1 and 2 through the openings 5 and 6, respectively, on centrifugation. Thus, they replace the deflectors 13.

What is claimed is:

1. A cuvette rotor, comprising:
   at least one radially extending cuvette for centrifuging samples about a central axis, the cuvette having first, second and third chambers respectively disposed radially from the central axis to a peripheral edge, the cuvette having a top wall, a bottom wall, and side walls;
   a first barrier projecting into the cuvette from the bottom wall and defining a boundary between the first and second chambers;
   a second barrier projecting into the cuvette from the bottom wall and defining a boundary between the second and third chambers;
   first, second and third ports disposed through the top wall of the cuvette above the first, second and third chambers, respectively;
   a first deflector disposed between the first and second ports, projecting into the cuvette from the top wall and connected to the top wall of the cuvette;
   a second deflector disposed between the second and third ports, projecting into the cuvette from the top wall and connected to the top wall of the cuvette;
   at least one vessel having top, bottom and side walls, the at least one vessel disposed arcuately around the central axis a predetermined distance from the at least one cuvette;
   at least one common side wall separating the at least one vessel from the at least one cuvette; and
   a fourth port disposed through the top wall of the at least one vessel.

2. A cuvette rotor as set forth in claim 1, wherein the at least one cuvette includes a plurality of cuvettes arcuately arranged about the central axis, and the at least one vessel includes a plurality of vessels arcuately arranged about the central axis.

3. A cuvette rotor as set forth in claim 2, wherein the cuvettes and the vessels are alternately arranged about the central axis, the vessels being located proximate the periphery of the rotor.

4. A cuvette rotor as set forth in claim 1, wherein the first and second defectors have substantially triangular cross-sections.

5. A cuvette rotor as set forth in claim 1, further comprising:
   first and second deflector walls extending to predetermined positions from the side walls of the cuvette, the first and second deflector walls extending from a radial location closer to the central axis than the second and third ports, respectively, the first and second deflector walls extending between and connecting the top and bottom walls of the cuvette.

6. A cuvette rotor as set forth in claim 1, wherein the third chamber includes first, second and third sub-chambers, the third sub-chamber having a cross-sectional area less than cross-sectional areas of the first and second sub-chambers, and being located closer to the periphery of the rotor than the first and second sub-chambers.

7. A cuvette rotor as set forth in claim 1, wherein at least one of the first and second deflectors includes means for deflecting, to a detector, a measurement ray focused thereon.

8. A cuvette rotor as set forth in claim 7, further including means disposed in the third chamber for permitting a measurement ray to be focused on said ray deflecting means.

9. A cuvette rotor, comprising:
   at least one radially extending cuvette for centrifuging samples about a central axis, the cuvette having first, second and third chambers respectively disposed radially from the central axis to a peripheral edge, the cuvette having a top wall, a bottom wall, and side walls;
   a first barrier projecting into the cuvette from the bottom wall and defining a boundary between the first and second chambers;
   a second barrier projecting into the cuvette from the bottom wall and defining a boundary between the second and third chambers;
   first, second and third ports disposed through the top wall of the cuvette above the first, second and third chambers, respectively;
   a first fluid deflector disposed between the first and second ports, projecting into the cuvette from the top wall and connected to the top wall of the cuvette; and
   a second fluid deflector disposed between the second and third ports, projecting into the cuvette from the top wall and connected to the top wall of the cuvette, the second fluid deflector including means for deflecting to a detector a light ray focused thereon.

* * * * *

UNITED STATES PATENT AND TRADEMARK OFFICE
CERTIFICATE OF CORRECTION

PATENT NO. : 5,186,896
DATED : February 16, 1993
INVENTOR(S) : Bernhard Bouchee, et. al.

It is certified that error appears in the above-indentified patent and that said Letters Patent is hereby corrected as shown below:

Column 4, line 6, change "defectors" to --deflectors--.

Signed and Sealed this

First Day of February, 1994

Attest:

BRUCE LEHMAN

*Attesting Officer*     *Commissioner of Patents and Trademarks*